United States Patent [19]

Saito et al.

[11] Patent Number: 4,985,140

[45] Date of Patent: Jan. 15, 1991

[54] APPARATUS FOR MEASURING FLASH POINT OF PETROLEUM INTERMEDIATE FRACTION AND METHOD FOR CONTROLLING FLASH POINT

[75] Inventors: Naohide Saito; Shohei Shibuya; Kentaro Inomata, all of Niigata, Japan

[73] Assignee: Nippon Oil Company, Ltd., Tokyo, Japan

[21] Appl. No.: 235,524

[22] Filed: Aug. 24, 1988

[30] Foreign Application Priority Data

Aug. 27, 1987 [JP] Japan ................................ 62-211247

[51] Int. Cl.[5] ................................................ B01D 3/42

[52] U.S. Cl. ............................. 208/347; 208/DIG. 1; 196/132; 203/3

[58] Field of Search ............... 208/350, 354, 355, 356, 208/DIG. 1, 347; 203/3; 196/132

[56] References Cited

U.S. PATENT DOCUMENTS 2,994,646 8/1961 Kleiss ............................. 196/132 X
3,156,628 11/1964 Larrison ................................. 203/3
3,177,138 4/1965 Larrison .......................... 196/132 X
3,301,778 1/1967 Cabbage ............................. 208/356
3,855,074 12/1974 Mosler et al. ....................... 203/3 X

*Primary Examiner*—Glenn Caldarola
*Attorney, Agent, or Firm*—Oblon, Spivak, McClelland, Maier & Neustadt

[57] ABSTRACT

There is here disclosed an apparatus for continuously measuring on an on-line system a flash point of an intermediate fraction such as kerosene in a petroleum distillation process from a difference between gas concentrations of the intermediate fraction at two predetermined temperatures; and a method for controlling the flash point of the intermediate fraction from the thus measured value.

2 Claims, 1 Drawing Sheet

G
1
2
2a
3
P
H
15
16
8
9
10
4
11
6
12
5
6a
7
13
14
7a

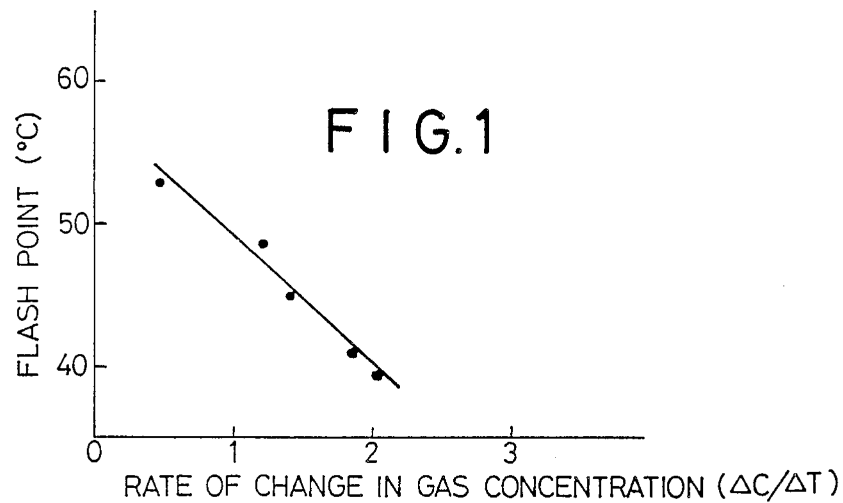
F I G. 1
FLASH POINT (°C)
60
50
40
0
1
2
3
RATE OF CHANGE IN GAS CONCENTRATION (ΔC/ΔT)
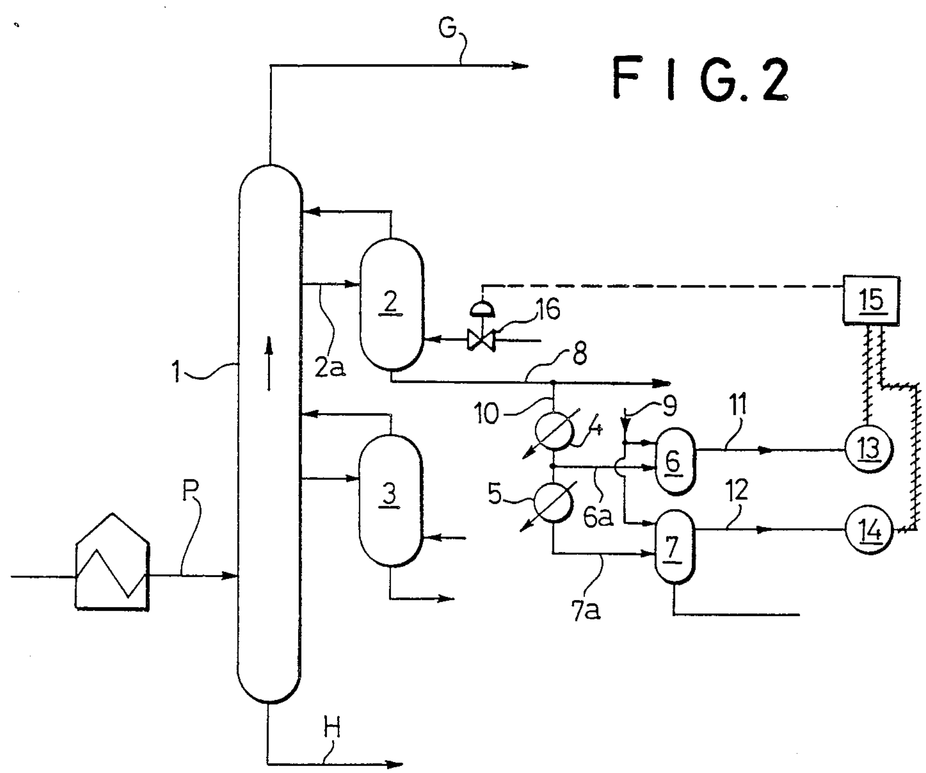
F I G. 2
G
1
2
2a
3
4
5
6
6a
7
7a
8
9
10
11
12
13
14
15
16
P
H

APPARATUS FOR MEASURING FLASH POINT OF PETROLEUM INTERMEDIATE FRACTION AND METHOD FOR CONTROLLING FLASH POINT

BACKGROUND OF THE INVENTION

1. Field of the Invention

The present invention relates to an on-line apparatus for measuring the flash point of a petroleum intermediate fraction such as kerosene during the distillation of crude oil, and it also relates to a method for controlling the flash point of the petroleum intermediate fraction by the utilization of the measured value obtained by the abovementioned measuring apparatus.

2. Description of the Prior Art

With regard to components of a gasoline fraction and an intermediate fraction such as kerosene of petroleum, their boiling points are continuously distributed, and therefore when these components are taken out from the crude oil by distillation, kerosene is stripped or heated with steam to vaporize volatile components therefrom, which volatile components are then delivered into a gasoline fraction, whereby the flash point of kerosene is adjusted.

In this case, if the flash point of kerosene is measured by an on-line system, the amount of the steam, for example, used for heating or stripping kerosene can be regulated on the basis of the measured value, so that the flash point can be stably maintained. However, such an on-line measuring apparatus has not been developed yet. Consequently, in general, kerosine is first sampled and its flash point is then measured directly on an off-line system, and the amount of the steam is controlled with the aid of operational experience making reference to a measured value. Accordingly, the accurate control of the steam amount to be used is difficult owing to time lag and the like. It is thus necessary to make a large allowance for the safe control, which obstructs the mass production of kerosene.

In a conventional known method for directly measuring a flash point by an on-line system, a certain amount of a liquid to be measured is first sampled, and a spark is emitted through a gaseous phase above the liquid during heating in order to inflame the gas. At this time, the occurred change is confirmed and measured by detecting the generation of sound or light.

In this method, since the liquid to be measured is sampled at certain time intervals, the continuous measurement is impossible. This conventional method is substantially identical with the off-line system.

Furthermore, there is known another method for indirectly measuring a flash point in which for example, a specific gravity or viscosity is measured and the flash point is then calculated from the interrelation between this factor and the flash point. In this case, needless to say, an on-line device for measuring the specific gravity or viscosity is required, and the measurement accuracy of the flash point depends upon the performance of the measuring device.

As discussed above, in a crude oil distillation process, any convenient and reliable device and method for detecting the flash point of the petroleum intermediate fraction such as kerosene by a continuous on-line system has not been heretofore established.

SUMMARY OF THE INVENTION

The present invention intends to solve the abovementioned problems. An object of the present invention is to provide an apparatus for measuring the flash point of a petroleum intermediate fraction simply and reliably by a continuous on-line system, and another object of the present invention is to provide a method for controlling the flash point of the intermediate fraction efficiently.

According to the present invention, the flash point of an intermediate fraction such as kerosene can be continuously measured in the distillation process of petroleum on an on-line system with the aid of a signal obtained by dividing a difference between gas concentrations of the intermediate fraction at two predetermined temperatures by a difference between the predetermined temperatures. Furthermore, the thus measured flash point of the intermediate fraction can heighten the extraction efficiency of volatile components for gasoline and the like from the intermediate fraction.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a graph illustrating the relation between rates of change in gas concentrations at oil temperatures of 30° to 40° C. and flash points of the oil; and FIG. 2 is a flow chart illustrating one embodiment of the present invention.

DETAILED DESCRIPTION OF THE PREFERRED EMBODIMENT

The inventors of the present application have researched as to whether or not a flash point of a liquid can be determined by heating the liquid and then measuring the rate of change in the amount or concentration of an inflammable gas above the liquid with respect to a temperature. As a result, it has been found that there is a definite interrelation between the flash point and the rate of change in the amount or concentration of the gas to the temperature. On the basis of this knowledge, the present invention which is quite novel has been achieved.

Describing the present invention in greater detail, a difference between the amounts or concentrations of the gas at two positions having predetermined temperatures is employed to obtain the rate of change of the temperature. Therefore, it is not always necessary to measure, the absolute amount of the gas.

The first aspect of the present invention is directed to an apparatus for measuring a flash point of a petroleum intermediate fraction which comprises a first device for measuring a first gas concentration at a first predetermined temperature of the intermediate fraction to provide a signal indicating the first gas concentration; a second device for measuring a second gas concentration at a second predetermined temperature, having a certain deviation from the first predetermined temperature, of the same intermediate fraction to provide a signal indicating the second gas concentration; a third device for dividing a difference between the first and second gas concentrations by a difference between the first and second predetermined temperatures to provide a signal; and a fourth device for making an arithmetical calculation based upon the signal from the third device in order to obtain a signal corresponding to the flash point of the intermediate fraction.

The second aspect of the present invention is directed to a method for controlling a flash point of a petroleum intermediate fraction which comprises the steps of measuring a first gas concentration at a first predetermined temperature of the intermediate fraction; measuring a second gas concentration at a second predetermined temperature having a certain deviation from the first predetermined temperature; dividing the difference between the first and second gas concentrations by the difference between the first and second predetermined temperatures so as to provide a first signal; making an arithmetical calculation based upon the first to provide a second signal; and utilizing the second signal to control feeding of a heat source such as stripping steam or oil for heating a fraction drawn from the bottom of a stripper or a fractionator for the intermediate fraction.

DESCRIPTION OF THE PREFERRED EMBODIMENT

Now, the present invention will be described, using kerosene as one example of a petroleum intermediate fraction in reference to accompanying dawings.

For various kerosene samples, gas concentrations in gaseous phases maintained at 30° C. and 40° C. were measured, and their rates of change K were then calculated. On the other hand, flash points of these kerosene samples were measured in a conventional manner. The interrelation between the rates of change and the flash points was determined to be as illustrated in FIG. 1. From the results in FIG. 1, the following formula (1) was obtained:

$$\text{Flash point} = 57 - 8.8\,K \ldots \qquad (1)$$

wherein rate of change $K = \Delta C/\Delta T$, and $\Delta C$ is a difference between measured concentrations and $\Delta T$ is a difference between measured temperatures.

Each temperature to be measured may be lower than the above-mentioned levels, but when it is too low, the amount of the vaporized gas is too small to measure its concentration.

The gas concentration (gas amount) was determined by first bringing the gas of the kerosene sample into contact with a coil-like platinum catalyst which was being heated, in order to burn it, and measuring the quantity of heat generated at this time.

The platinum coil and another similar platinum coil which had not been heated were used in the form of a pair to constitute a Wheatstone bridge circuit, and when the temperature of the coil was raised by the generated heat, electric resistance of the coil correspondingly changed. From a, in the voltage of the coil changed its electric resistance, the gas amount or concentration was determined.

Two measuring devices of this type were simultaneously employed, and the gas concentration in the gaseous phase of the kerosene sample maintained at 30° C. was measured by the use of one detector means (the Wheatstone bridge circuit). On the other hand, the gas concentration in the gaseous phase of the kerosene sample maintained at 40° C. was measured by the other detector means in order to obtain basic data for the above-mentioned formula (1).

FIG. 2 shows a flow sheet illustrating one embodiment of the present invention. In this drawing, there is shown a crude oil distillation column 1, a kerosene stripper 2, a gas oil stripper 3, a first cooler 4 for setting a temperature, a second cooler 5 for setting a temperature, a first pot 6 for the gaseous sample, a second pot 7 for the gaseous sample, a kerosene extraction line 8, an air line 9, a kerosene sampling line 10, a first gas sample line 11, and second gas sample line 12. Also shown is a first detector 13 of the amount of gas, a second detector 14 of the amount of gas, an arithmetical unit 15, and a steam control valve 16. In this drawing, crude oil was fed to the distillation column 1 as indicated by an arrow P, and the crude oil was then distilled in the column 1. Afterward, gas oil for gasoline was extracted from the top of the distillation column 1 as indicated by an arrow G and residual oil containing heavy oil, pitch and the like was discharged from the bottom thereof as indicated by an arrow H. At an upper position in the middle portion of the distillation column 1, there was provided a kerosene stripper 2. Kerosene was delivered to this kerosene stripper 2 through a kerosene pipe 2*a*, and the kerosene was then extracted through a kerosene extraction line 8. Under the kerosene stripper 2, a gas oil stripper 3 was disposed to the distillation column 1.

A kerosene sampling line 10 was connected to the extraction line 8, and on the sampling line 10, and the first cooler 4 and the second cooler 5 for setting temperatures of the kerosene portions to predetermined levels were mounted. The kerosene portion which had been set to 40° C. by means of the first cooler 4 was fed via a line 6*a* to a first pot for the gaseous sample, and the kerosene portion which had been set to 30° C. by means of the second cooler 5 was fed via a line 7*a* to a second pot 7 for the gaseous sample. To the first and second pots 6 and 7, air was fed through an air line 9, and gases generated in both the pots 6 and 7 were forwarded to the first gas amount detector 13 and the second gas amount detector 14 via gaseous sampling lines 11 and 12, respectively. That is, the gas generated from the kerosene set to 30° C. was delivered to the first gas amount detector 12, and the gas generated from the kerosene set to 40° C. was delivered to the second gas amount detector 14.

As described above, the first and second gas detectors 13, 14 were the Wheatstone bridge circuits each comprising a platinum catalyst which was being heated and another similar platinum catalyst which was not heated. These detectors 13, 14 detected the gas concentrations, and the data from them were inputted into an arithmetical unit 15. The above detection of the gas concentrations was continuously carried out by an on-line system. In the arithmetical unit 15, the difference between both the gas concentrations indicated by the first and second data signals of the gas concentrations delivered from the first and second gas detectors 13, 14 was divided by a difference between both the predetermined temperatures (30° C. and 40° C.) in order to obtain a third signal (see FIG. 1). This signal was subjected to an arithmetical calculation by the arithmetical unit 15 in order to provide a fourth signal corresponding to a flash point of the kerosene in the kerosene stripper 2. Furthermore, this output corresponding to the flash point of the kerosene was forwarded to steam control valve 16 in order to control the feed of steam for heating the fraction drawn from the bottom of the kerosene stripper 2, so that the flash point of the kerosene was controlled.

The apparatus and the controlling method described above are applicable to control the feed of the heat source for fractionators other than the kerosene stripper. In the above embodiment, the method of controlling the flash point of kerosene has been described, but the present invention can also be applied to the flash point control of gas oil.

Obviously, numerous modifications and variations of the present invention are possible in light of the above teachings. It is therefore to be understood that within the scope of the appended claims, the invention may be practiced otherwise than as specifically described herein.

What is claimed is:

1. An apparatus for measuring a flash point of a petroleum intermediate fraction which comprises:

a first device for measuring a first gas concentration at a first predetermined temperature of the intermediate fraction so as to provide a first signal indicating the first gas concentration;

a second device for measuring a second gas concentration at a second predetermined temperature, having a certain deviation from the first predetermined temperature, of the intermediate fraction so as to provide a second signal indicating the second gas concentration;

a third device for generating a third signal representative of the difference between the first and second gas concentration divided by a difference between the first and second predetermined temperatures; and a fourth device for obtaining a fourth signal determined by an arithmetical calculation based on the third signal from the third device wherein said fourth signal corresponds to the flash point of the intermediate fraction.

2. A method for controlling a flash point of a petroleum intermediate fraction which comprises:

generating a first signal based upon measuring the concentration of a first gas at a first predetermined temperature of the intermediate fraction;

generating a second signal based upon measuring the concentration of a second gas at a second predetermined temperature having a certain deviation from the first predetermined temperature;

dividing a difference between the first and second signals based upon first and second gas concentrations by a difference between the first and second predetermined temperatures so as to obtain a third signal; p1 performing an arithmetical calculation of the third signal so as to provide a fourth signal; and utilizing said fourth signal to control feeding of a heat source based upon said fourth signal for heating a fraction drawn from the bottom of a stripper or a fractionator for the intermediate fraction.

* * * * *